United States Patent
Niles et al.

(10) Patent No.: US 7,191,776 B2
(45) Date of Patent: *Mar. 20, 2007

(54) NEBULIZER BREATHING SYSTEM

(75) Inventors: Rex A. Niles, Oneida, NY (US);
Richard K. Pelerossi, Rome, NY (US);
Fredrick M. Richards, Clinton, NY (US)

(73) Assignee: Smiths Medical ASD, Inc., Keene, NH (US)

( * ) Notice: Subject to any disclaimer, the term of this patent is extended or adjusted under 35 U.S.C. 154(b) by 2 days.

This patent is subject to a terminal disclaimer.

(21) Appl. No.: 10/842,334

(22) Filed: May 10, 2004

(65) Prior Publication Data

US 2005/0247313 A1    Nov. 10, 2005

(51) Int. Cl.
*A61M 11/00* (2006.01)
*A61M 16/00* (2006.01)

(52) U.S. Cl. .............................. 128/200.14; 128/200.11; 128/203.12

(58) Field of Classification Search .............................
128/200.14–200.24, 203.12, 203.16, 201.28,
128/203.11, 205.13, 205.24, 204.18, 207.14–18,
128/200.11, 202.27; 239/338, 352; D24/110–110.6;
261/78.1; D28/91.1
See application file for complete search history.

(56) References Cited

U.S. PATENT DOCUMENTS

| | | | |
|---|---|---|---|
| 3,667,463 A | 6/1972 | Barnes | |
| 3,874,379 A | 4/1975 | Enfield et al. | |
| 4,767,576 A | 8/1988 | Bagwell et al. | |
| 5,099,833 A * | 3/1992 | Michaels | 128/200.14 |
| 5,277,175 A * | 1/1994 | Riggs et al. | 128/200.21 |
| 5,355,872 A * | 10/1994 | Riggs et al. | 128/200.21 |
| 5,586,551 A * | 12/1996 | Hilliard | 128/203.29 |
| 5,701,886 A * | 12/1997 | Ryatt | 128/203.12 |
| 6,041,776 A | 3/2000 | Briggs, III et al. | |
| RE38,700 E * | 2/2005 | Briggs, III | 128/200.21 |
| 7,036,500 B2* | 5/2006 | Niles et al. | 128/200.14 |
| 2005/0235985 A1* | 10/2005 | Niles et al. | 128/200.14 |

FOREIGN PATENT DOCUMENTS

WO    WO 03/049791    6/2003

* cited by examiner

*Primary Examiner*—Teena Mitchell
*Assistant Examiner*—Shumaya Ali
(74) *Attorney, Agent, or Firm*—August E. Roehrig, Jr.; Luedeka, Neely & Graham, P.C.

(57) ABSTRACT

An improved nebulizer breathing system wherein a supplemental gas may be introduced into the nebulizer head at a position after the liquefied medication has been fractured or nebulized, so that the introduction of the supplemental gas does not effect the rate at which the nebulized liquefied medication is applied to the user, and the mixture of gases to be administered to a patient is added to the breathing system at a position removed from the point at which the gas mixture is administered to the patient.

16 Claims, 2 Drawing Sheets

NEBULIZER BREATHING SYSTEM

FIELD OF THE INVENTION

Figure 1:
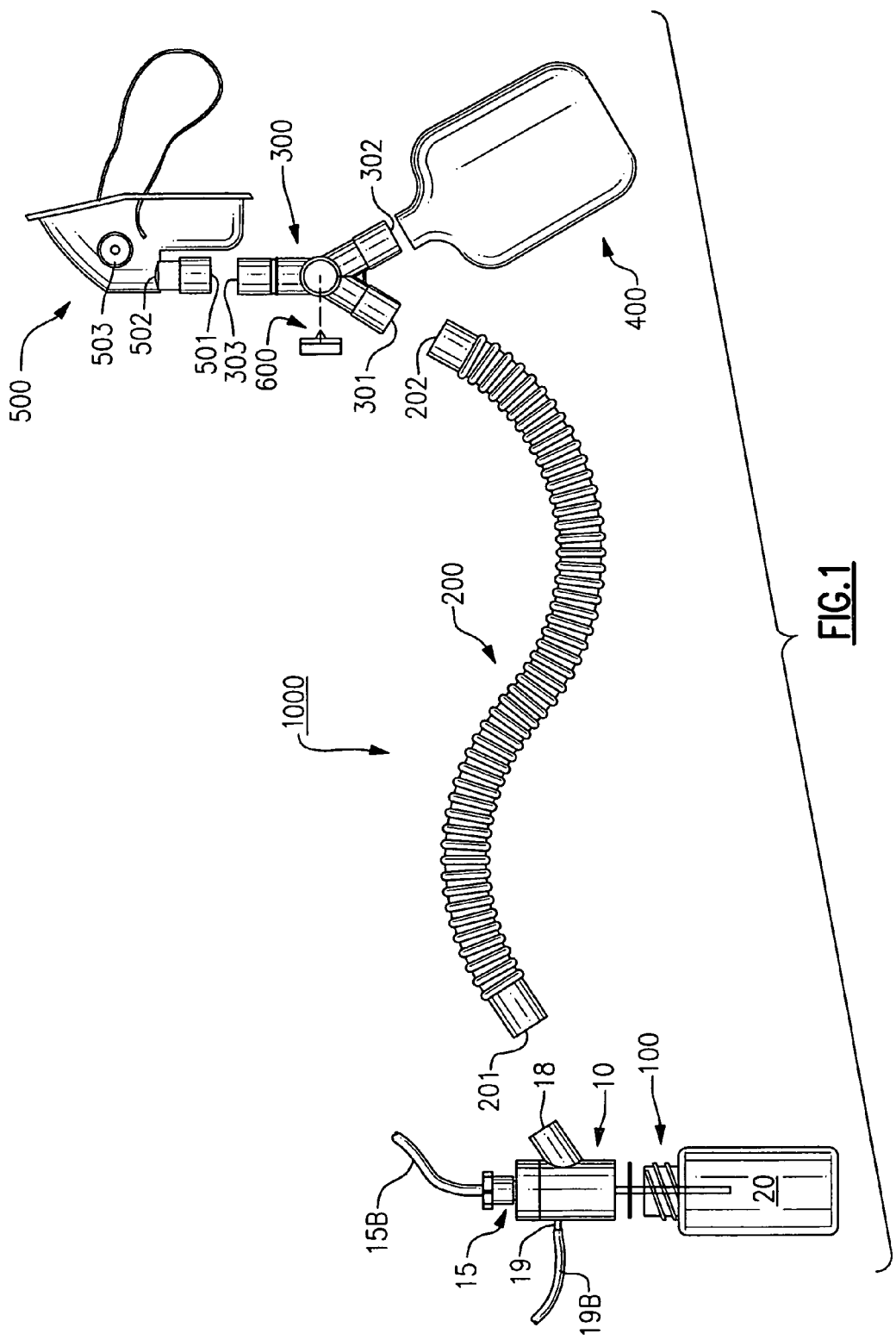
Figure 2:
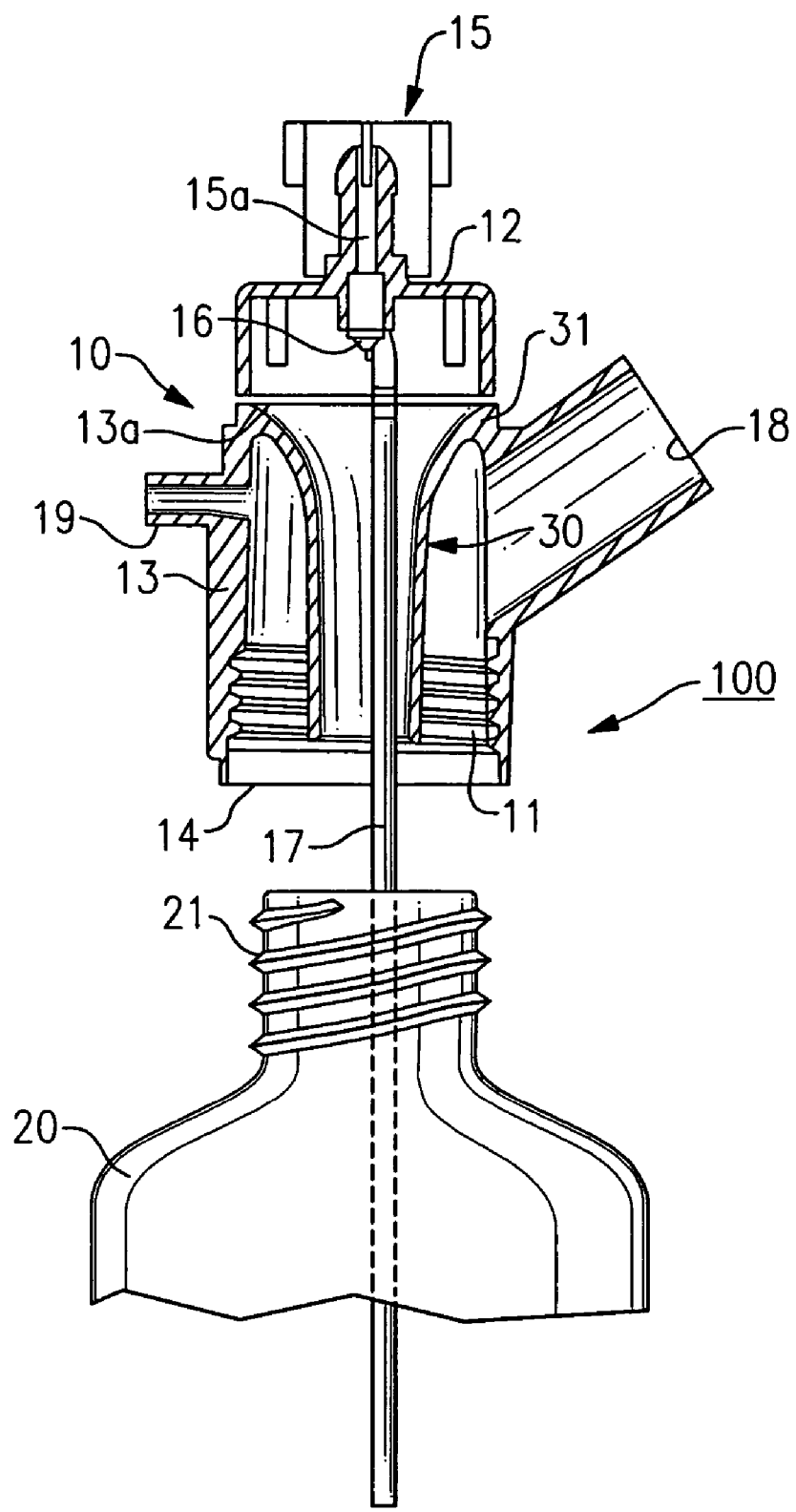

This invention relates in general to an improved breathing system incorporating a nebulizer and, in particular, to an improved breathing system including a non-rebreather mask, a reservoir bag, a rescue valve and an improved nebulizer having an auxiliary gas port carried by a nebulizer head in a position removed from the nebulization chamber to introduce an auxiliary gas into the nebulizer head, when desired, without effecting the rate at which the breathing system applies medication to the nebulizer user.

BACKGROUND OF THE INVENTION

Persons requiring treatment of certain kinds of respiratory conditions frequently need to have medications delivered directly to the lungs. Nebulized or aerosolized solutions are the preferred method of delivery of respiratory medication because the medicant is fragmented into small particles that are more efficiently deposited near sites of drug activity in the lungs.

While nebulizers are well known to those skilled in the art, aerosolization of medications in a nebulizer is effected by putting a liquefied medication into a container or liquid reservoir and introducing a pressurized flow of gas through an aerosol nozzle carried within a nebulization chamber which is coupled to the liquefied medication contained in the liquid reservoir by a liquid draw tube. As the pressurized high velocity gas flows through the aerosol nozzle, the liquefied medication is drawn through the liquid draw or aspirator tube into the path of the high velocity gas and is fractured thereby into a mist, becoming entrained with the gas flow out of the nebulization chamber through the container and out therefrom through an output port.

In certain applications, nebulization therapy can be enhanced through the use of an auxiliary gas to supplement the nebulizing or driving gas being introduced through the aerosol nozzle. Such supplemental gases may be air, oxygen, helium or a combination of these two gases, referred to as heliox, depending upon the particular driving gas being used. The use of helium, an inert and metabolically stable gas which readily diffuses into swollen airways, or heliox, as a supplement to the nebulizing gas is also known, and these gasses are frequently used to drive the nebulized medication deeper into a user's lungs to deliver medications to bypass obstructed or restricted airways for a greater and more rapid effect from the medication.

One of the problems encountered when using supplemental gases, however, is that the injection of the supplemental gas into the nebulizing gas or into the nebulizing chamber affects the rate at which the liquefied medication passes out from the container through the aerosol output port. Generally, the rate at which the liquefied medication is to be nebulized and delivered to the user, is determined based upon, among other factors, the rate of flow and density of the driving or nebulizing gas being introduced into the nebulization chamber. When a supplemental gas is introduced into the nebulizing gas flow or into the nebulization chamber, the total quantity of medication delivered through the nebulization chamber changes. Accordingly, the predetermined rate at which the liquefied medication is discharged through the aerosol output port varies from that at which it was initially set.

Another problem encountered when a supplemental gas is introduced into a nebulizer breathing system, is that the supplemental gas is introduced at a point in the system close to the patient interface, such as a non-rebreathing (NRB) mask. The introduction of a supplemental gas at such a position relative to the NRB mask frequently results in the application of a non-uniform gas mixture. If a patient does not take uniform breaths, or the patient's breathing pauses, the percentage of the supplemental gas being introduced increases, or spikes, resulting in the patient inhaling a greater percentage of the supplemental gas with the next breath.

SUMMARY OF THE INVENTION

The present invention is directed to overcoming one or more of the problems or disadvantages associated with the relevant technology. As will be more readily understood and fully appreciated from the following detailed description of a preferred embodiment of the present invention, the invention is embodied in an improved nebulizer breathing system wherein a supplemental gas may be introduced into the nebulizer head at a position after the liquefied medication has been fractured or nebulized, so that the introduction of the supplemental gas does not effect the rate at which the nebulized liquefied medication is applied to the user, and the mixture of gases to be administered to a patient is added to the breathing system at a position removed from the point at which the gas mixture is administered to the patient.

DESCRIPTION OF THE DRAWINGS

Further objectives of the invention, together with additional features contributing thereto and advantages accruing therefrom, will be apparent from the following description of a preferred embodiment of the invention which is shown in the accompanying drawings, wherein:

FIG. 1 illustrates an exploded view of the improved nebulizer breathing system of the invention; and FIG. 2 is an elevational view of a component of the invention with portions broken away to better illustrate the internal construction thereof.

DETAILED DESCRIPTION OF A PREFERRED EMBODIMENT

Referring now to the drawings, there is illustrated in FIG. 1 a preferred embodiment of the improved nebulizer breathing system 1000 which includes a nebulizer 100, a flexible tubing 200 connecting at a first inlet end to the output port of the nebulizer and at a second outlet end to the remainder of the breathing system, a wye 300 connected at a first input branch to the outlet end of the flexible tubing and having a second input branch and a discharge outlet, a flexible reservoir bag 400 having an outlet connected to the second input branch of the wye, a NRB mask 500 having an inlet connected to the discharge outlet of the wye, and a rescue valve 600 carried by the wye to permit a patient to inhale through the mask in the event the patient is beginning to draw a negative pressure or vacuum.

The nebulizer 100, illustrated in detail in FIG. 2, is preferably molded from translucent plastic and includes a nebulizer head 10 which is adapted to be received on a liquid container or receptacle 20. To this end, the lowermost portion of the nebulizer head 10 is open and formed with an internal thread 11 which is sized to receive a complementary external thread 21 formed on the top or neck portion of the liquid receptacle 20 for forming a liquid-tight seal.

The nebulizing head 10 has a closed circular-shaped top 12 and a depending skirt 13 forming a generally cylindrical shape with an open bottom 14 adapted to receive the liquid container 20. A nebulization chamber 30 is formed inside the nebulization head 10 and spaced downwardly from the top 12. The nebulization chamber 30 extends downwardly from a point of attachment 31 on the inner wall 13a of the skirt 13 towards the open end 14 of the nebulizer head, forming a chamber in which the liquid contained in the liquid container 20 is entrained in a driving or nebulizing gas introduced through the top 12 of the nebulizer head 10 into the nebulization chamber 30.

The top 12 of the nebulizer head 10 supports an adapter 15 by which a suitable source of driving or nebulizing gas is connected, such as by a flow meter or tubing 15b, for introduction into the nebulizing chamber 30. A conventional nebulizing nozzle 16 is supported within the nebulizing chamber 30 beneath the top 12, and is coupled to a passageway 15a formed through the adapter 15 by which the driving or nebulizing gas is introduced into the nebulizing chamber 30. The nebulizing nozzle 16 communicates with a suitable orifice at an upper terminal end of an aspirator tube 17 which extends downwardly into the liquid medicant contained in the liquid receptacle 20. In this manner, when a source of driving or nebulizing gas is coupled to the adapter 15, and introduced to the nebulizing nozzle 16, the liquid medicant contained within the receptacle 20 will be entrained in the driving or nebulizing gas and discharged out from the nebulizer chamber 30. The entrained aerosol so formed will then pass through the nebulizing head 10 to be discharged from the nebulizer 100 through a nebulized aerosol discharge outlet 18, formed through the sidewall 13, and into the flexible tubing 200.

To provide for the introduction of a supplemental gas into the nebulizer 100, an auxiliary gas inlet port 19 is formed in the side wall 13 at a point preferably opposite to the nebulized aerosol discharge outlet 18. The auxiliary gas inlet port 19 is coupled to a suitable source of supplemental gas, such as oxygen, helium or heliox, by tubing 19b and the inlet port extends into the nebulizing head 10, but not into the nebulizer chamber 30. In this manner the supplemental gas introduced through inlet port 19 will not affect the rate at which the aerosolized medicant is delivered from port 18. As heretofore described, when a supplemental gas is introduced into the driving or nebulizing gas, or the nebulizing chamber 30, the supplemental gas so introduced effects the uniformity of the administration of the medication. When a supplemental gas is so introduced, the rate of medication application increases with the increased gas flow. By introducing the supplemental gas through the auxiliary gas inlet port 19, the supplemental gas does not change the rate at which medication exiting the nebulizer through port 18 is applied to the nebulizer user. When a source of supplemental gas is not being introduced through auxiliary gas inlet port 19, a conventional cap, not shown, may be placed over the external opening thereto.

When the medication containing gas mixture exits the nebulizer 100 through the discharge or output port 18, the gas passes into the first inlet end 201 of the flexible tubing 200. The flexible tubing is preferably a collapsible type of flexible tubing such as that commercially available and sold under the trademark "POPPLE". The second outlet end 202 of the flexible tubing 200 is connected to a first input branch 301 of a wye connector 300 to space the output of the gas mixture from the nebulizer 100 a distance away from the inlet to a NRB mask 500 through which a patient breathes the medicant-containing mixture. Preferably, the flexible tubing 200 is at least approximately 18 inches in length, and can be approximately 72 inches in length, to create a mixture that when inhaled by the user will be more uniform, than systems wherein a supplemental gas is administered to the user by means of a supplemental gas source connected to or substantially adjacent to the NRB mask 500, or connected to or substantially adjacent the wye connector 300.

A flexible bag reservoir 400 is connected in fluid communication to a second input branch 302 of the wye connector 300, and functions as an accumulator which holds enough of the incoming gas mixture to compensate for the patient's next breath in the event of over-breathing, as is known to those skilled in the respiratory care art.

The NRB mask 500 is sized to fit to the patient's face, and encompass the nose and mouth thereof. Such masks, or the equivalents thereof, are available in different sizes to accommodate patients from pediatric through adults. The mask 500 has an inlet 501 connected to a discharge outlet 303 of the wye 300. Conventional one-way inhalation 502 and one-way exhalation valves 503, one of which is shown, are carried in the NRB mask. The inhalation valve 502 is open during patient inhalation, and closes during patient exhalation. However, during periods of patient inactivity, the inhalation valve 501 may stay open because of the positive pressure coupled thereto by the nebulizer 100. The valve, however, prevents exhaled breath from traveling back into the wye 300. The exhalation valves 503 open during exhalation, and close during inhalation. In this manner, the expiratory air discharged by a patient is exhausted to atmosphere, and does not go back into the breathing system.

In order to ensure that a patient does not draw a negative pressure in the system in the event the patient is over-breathing, a conventional rescue valve 600 is incorporated into the wye 300. The rescue valve 600 is a one-way inhalation valve which is normally closed, but when a patient over-breathes the nebulizer system, the rescue valve 600 will open permitting the patient to breathe ambient air through the rescue valve, and preventing the patient from drawing a negative pressure or vacuum. When the patient is normally breathing, and does not over breath the system, the rescue valve 600 will remain closed.

While this invention has been described in the specification and illustrated in the drawings with reference to a preferred embodiment, the structure of which has been disclosed herein, it will be understood by those skilled in the art to which this invention pertains that various changes may be made and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

What is claimed is:

1. A nebulizer breathing system comprising:
   a nebulizer having a nebulizer head adapted to be received on a receptacle adapted to contain a liquid medicant to be nebulized;
   said nebulizer head including a first chamber having a closed top, enclosing sides and an open bottom adapted to receive for coupling thereto a receptacle adapted to contain a liquid medicant to be dispensed at a predetermined rate of concentration;

said nebulizer bead including a second nebulizing chamber carried within said first chamber at a position spaced from said closed top and extending downwardly therefrom;

said nebulizing chamber having an open bottom adapted to pass entrained and nebulized liquid medicant outwardly there through;

a nebulizing nozzle in fluid communication with said nebulizing chamber for creating a nebulized aerosol from liquid medicant coupled thereto;

means for coupling a flow of nebulizing gas into said first chamber to said nebulizing nozzle and through said second nebulizing chamber carried within said first chamber;

an aspirator tube having a first end positioned in fluid communication adjacent to said nebulizing nozzle, and a second end positioned to be received into liquid medicant contained within the receptacle;

an auxiliary gas inlet port for introducing a supplemental gas into said first chamber extending into said first chamber at a position removed from the interior of said nebulizing chamber;

said first chamber having a discharge outlet spaced from said open bottom of said nebulizing chamber and said auxiliary gas inlet port, for discharging liquid medicant entrained in said nebulizing chamber and the supplemental gas introduced into said first chamber through said auxiliary gas inlet port from said nebulize; and a flexible tube coupled to said nebulizer discharge outlet and extending there from, said flexible tube having a discharge outlet for connecting the entrained liquid medicant discharged from said nebulizer discharge outlet to a patient interface;

said flexible tube extending a length sufficient to provide a substantially uniform entrained liquid medicant discharge to the patient interface.

2. The nebulizer breathing system of claim 1 wherein said patient interface comprises a non-rebreathing mask for receiving the entrained liquid medicant discharged from said flexible tube.

3. The nebulizer breathing system of claim 2 wherein said non-rebreathing mask includes a valve which opens upon inhalation and closes upon exhalation, and a valve which opens upon exhalation and closes upon inhalation.

4. The nebulizer breathing system of claim 2 further including a reservoir for accumulating a quantity of entrained liquid medicant discharged from said flexible tube for discharge to said non-rebreathing mask in response to a patient's breathing.

5. The nebulizer breathing system of claim 2 further including a normally closed rescue valve which is opened in response to a patient over-breathing the quantity of the entrained liquid medicant discharged from said flexible tube to said non-rebreathing mask.

6. The nebulizer breathing system of claim 2 further including:

a wye having a first inlet connected to the outlet of said flexible tube, a second inlet and a discharge outlet;

a reservoir for accumulating a quantity of entrained liquid medicant discharged from said flexible tube, said reservoir being connected to said second inlet of said wye; and said non-rebreathing mask being connected to said discharge outlet of said wye.

7. The nebulizer breathing system of claim 6 wherein said wye further includes a normally closed rescue valve which is opened in response to a patient over-breathing the quantity of entrained liquid medicant discharged from said flexible tube to said non-rebreathing mask.

8. The nebulizer breathing system of claim 1 wherein said auxiliary gas inlet port and said discharge outlet are in opposed positions relative to each other, and said nebulizing chamber carried within said first chamber extends therebetween.

9. The nebulizer breathing system of claim 8 wherein said nebulizing chamber has a open top attached to the interior of said first chamber at a position above said auxiliary gas inlet port and said nebulizing chamber extends downwardly therefrom such that said open bottom of said nebulizing chamber is positioned at a location removed from said auxiliary gas inlet port.

10. The nebulizer breathing system of claim 8 wherein said nebulizing nozzle is supported from said first chamber top above said nebulizing chamber for entraining liquid medicant communicated thereto through said aspirator tube.

11. The nebulizer breathing system of claim 8 wherein said nebulizing chamber extends downwardly within said first chamber such that said open bottom of said nebulizing chamber is positioned at a location below said auxiliary gas inlet port and below said first chamber discharge outlet.

12. The nebulizer breathing system of claim 1 further including a receptacle for containing liquid medicant to be dispensed through said discharge outlet.

13. The nebulizer breathing system of claim 12 wherein said receptacle includes means for releasibly connecting said receptacle to said first chamber in sealing engagement therewith.

14. The nebulizer breathing system of claim 1 wherein said means for coupling a flow of nebulizing gas into said first chamber comprises an adapter for releasably coupling a source of driving gas to said nebulizing nozzle.

15. The nebulizer breathing system of claim 1 wherein said auxiliary gas inlet port includes means for selectively closing said auxiliary gas inlet port when not in use.

16. A method of delivering a liquid medicant entrained in a selected mixture of gases in a substantially uniform manner, comprising:

passing a flow of driving gas into a nebulizer chamber of a nebulizer for fracturing medicant contained therein and creating a medicant aerosol in said nebulizer chamber;

introducing a supplemental gas into said nebulizer at a location removed from said nebulizer chamber thereby mixing said supplemental gas with said medicant aerosol from said nebulizer chamber, without effecting the rate at which medicant is delivered from said nebulizing chamber to a nebulizer user;

discharging said mixture of said medicant aerosol nebulized by said driving gas in said nebulizer chamber, and said supplemental gas, from said nebulizer into a flexible tube; and passing said aerosolized medicant mixture through said flexible tube to a breathing mask for a distance sufficient to maintain a substantially uniform mixture of aerosolized medicant at said breathing mask.

* * * * *

UNITED STATES PATENT AND TRADEMARK OFFICE
CERTIFICATE OF CORRECTION

| | |
|---|---|
| PATENT NO. | : 7,191,776 B2 |
| APPLICATION NO. | : 10/842334 |
| DATED | : March 20, 2007 |
| INVENTOR(S) | : Rex A. Niles, Richard K. Pelerossi and Fredrick M. Richards |

It is certified that error appears in the above-identified patent and that said Letters Patent is hereby corrected as shown below:

At Col. 5, Claim 1, Line 28, after "said auxiliary gas inlet port from said", delete "nebulize" and insert --nebulizer--.

Signed and Sealed this

Twenty-sixth Day of June, 2007

JON W. DUDAS
*Director of the United States Patent and Trademark Office*